(12) United States Patent
Weidner et al.

(10) Patent No.: US 9,023,615 B2
(45) Date of Patent: May 5, 2015

(54) GRAM STAINING METHOD WITH IMPROVED DECOLORIZATION OF THE CRYSTAL VIOLET-IODINE COMPLEX FROM GRAM NEGATIVE BACTERIA

(71) Applicant: Ventana Medical Systems, Inc., Tucson, AZ (US)

(72) Inventors: Charles Weidner, Tucson, AZ (US); Cynthia Connolly, Tucson, AZ (US); Lesley Schumack, Tucson, AZ (US); Parula Mehta, Oro Valley, AZ (US); Setareh Duquette, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/773,864

(22) Filed: Feb. 22, 2013

(65) Prior Publication Data

US 2013/0244252 A1    Sep. 19, 2013

Related U.S. Application Data

(60) Provisional application No. 61/612,520, filed on Mar. 19, 2012.

(51) Int. Cl.

| | | |
|---|---|---|
| *G01N 1/30* | (2006.01) | |
| *G01N 33/48* | (2006.01) | |
| *C12Q 1/00* | (2006.01) | |
| *C12M 1/00* | (2006.01) | |
| *C12M 3/00* | (2006.01) | |
| *G01N 1/31* | (2006.01) | |
| *C12Q 1/04* | (2006.01) | |

(52) U.S. Cl.
CPC . *G01N 1/312* (2013.01); *C12Q 1/04* (2013.01)

(58) Field of Classification Search
None
See application file for complete search history.

(56) References Cited

U.S. PATENT DOCUMENTS

| | | | |
|---|---|---|---|
| 5,180,606 A * | 1/1993 | Stokes et al. | 427/2.13 |
| 6,352,861 B1 | 3/2002 | Copeland et al. | |
| 6,521,028 B1 * | 2/2003 | Frenier | 106/14.42 |

FOREIGN PATENT DOCUMENTS

| | | | |
|---|---|---|---|
| CN | 1 392 266 A | 1/2003 | |
| EP | 2 022 858 A1 | 2/2009 | |
| JP | 58 020198 A | 2/1983 | |
| WO | WO 2010/080287 A1 | 7/2010 | |
| WO | WO 2010114858 A1 * | 10/2010 | F15C 3/00 |

OTHER PUBLICATIONS

Garvey, A reliable method for demonstrating Gram-Positive and Gram-Negative Bacteria, Biotech Histochem, 61(4), 251-253, 1986.*
Burke, Notes on the Gram Stain with Description of a New Method, Journal of Bacteriology, 7(2), 159-182, 1921.*
Whitman et al., Isolation of Psychrophilic Bacteriophage Host Systems from Refrigerated Food Products, Appl. Microbiol. 1971, 22(2):220-223.*
European Patent Office, International Search Report and Written Opinion mailed on Apr. 19, 2013 for International Application No. PCT/EP2013/053510.

* cited by examiner

*Primary Examiner* — Galina Yakovleva
*Assistant Examiner* — Andrea S Grossman
(74) *Attorney, Agent, or Firm* — Klarquist Sparkman, LLP

(57) ABSTRACT

Provided herein are methods of staining biological material for the purpose of detecting, and in some examples also identifying, microorganisms. Methods of Gram staining bacteria using a slow-acting decolorizing formulation, such as one that includes 1,2-propandiol or ethylene glycol, can be used to extend the time of the decolorizing step, and thus permit automation of the Gram staining method. Also provided are compositions and kits for performing automated Gram staining on microscope slides.

18 Claims, 1 Drawing Sheet

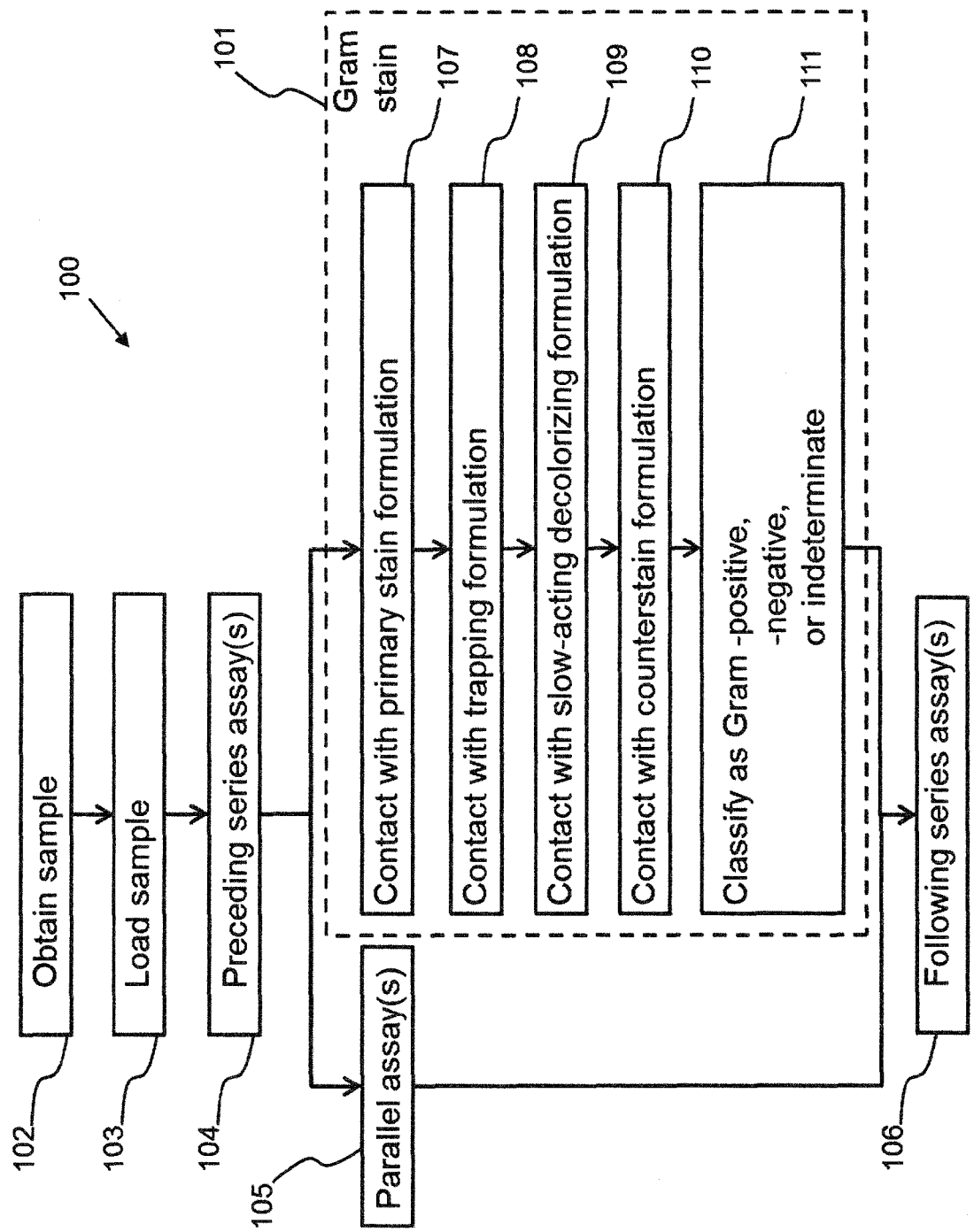

GRAM STAINING METHOD WITH IMPROVED DECOLORIZATION OF THE CRYSTAL VIOLET-IODINE COMPLEX FROM GRAM NEGATIVE BACTERIA

CROSS-REFERENCE TO RELATED APPLICATION

This application claims priority to U.S. Provisional Application No. 61/612,520 filed Mar. 19, 2012, herein incorporated by reference.

FIELD

The present disclosure relates to methods of staining biological material for the purpose of detecting, and in some examples also identifying, microorganisms. More particularly, the present disclosure relates to methods, compositions, and kits for performing automated Gram staining on microscope slides.

BACKGROUND

The Gram stain is a well-known, commonly used microbiological technique for the detection, classification, and identification of microorganisms, especially bacteria. The most common method of the Gram staining involves four steps: staining, trapping, decolorizing, and counterstaining. The Gram stain as commonly used in histology laboratories is known to be inconsistent, in particular, as a result of variability in the decolorizing step. Variables affecting the decolorizing step include solvent strength, concentration, volume, and duration of exposure. During manual Gram staining procedures, the decolorizing step routinely uses alcohol or acetone, and the step only takes a matter of seconds. However, for automated staining procedures, this decolorizing process occurs too quickly. This disclosure addresses the issues of Gram stain decolorizing on an automated staining platform.

SUMMARY

Provided herein are methods, compositions, and kits that permit automation of Gram staining. The inventors have identified compositions that prolong the decolorizing step of Gram staining, which permits automation of Gram staining, for example, using automated and/or computer-implemented staining equipment.

Methods are provided for Gram staining a sample, such as a sample on a microscope slide. Such methods can be used to detect and distinguish Gram-positive and Gram-negative bacteria. In some examples, the disclosed Gram staining methods are used to detect non-bacterial microorganisms, such as yeast (e.g., *Candida* and *Cryptococcus*).

In particular examples, the methods include contacting the sample with a slow-acting decolorizing formulation (such as one that includes 1,2-propanediol or ethylene glycol) under conditions sufficient to significantly remove a primary stain-trapping agent complex from Gram-negative bacteria, but not from Gram-positive bacteria. The sample is one that was previously contacted with a primary stain (such as crystal violet) and a trapping agent (such as iodine). In particular examples, the methods include one or more additional steps of the Gram staining procedure, such as contacting the sample with the primary stain under conditions sufficient to stain the cell wall and cell membrane of Gram-positive and Gram-negative bacteria; contacting the sample with a trapping agent under conditions sufficient to form a primary stain-trapping agent complex; contacting the sample with a counterstain under conditions sufficient to stain decolorized Gram-negative bacteria, or combinations thereof.

Also provided are compositions that can act as a slow-acting decolorizing formulation. In one example, the composition includes at least 80% of a slow-acting decolorizing agent (such as 1,2-propanediol or ethylene glycol) and no more than 20% of a fast-acting decolorizing agent (such as 0.1 to 20% of a fast-acting decolorizing agent, for example ethyl alcohol or acetone). Such compositions can be used as the slow-acting decolorizing formulation in an automated Gram stain.

Kits for automated Gram staining are also provided. In one example, the kit includes a slow-acting decolorizing formulation in a container, such as a formulation that includes at least 80% or at least 90% of a slow-acting decolorizing agent (such as 1,2-propanediol or ethylene glycol) and no more than 20% of a fast-acting decolorizing agent (such as 0.1 to 20% or 1 to 10% of a fast-acting decolorizing agent, for example ethyl alcohol or acetone). In some examples, kits can additionally include other components, such as one or more of a primary stain in a container, a trapping agent in a container, a counterstain in a container, microscope slides, coverslips, other stains, and control slides. In particular examples, the container is configured to be used with an automated Gram staining platform.

The foregoing and other objects and features of the disclosure will become more apparent from the following detailed description, which proceeds with reference to the accompanying figure.

BRIEF DESCRIPTION OF THE DRAWING

FIG. 1 is a flow chart showing an exemplary method for automated Gram staining.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. In case of conflict, the present specification, including explanations of terms, will control. Explanation of common terms and methods in microbiology may be found in Wistreich and Lechtman, Laboratory Exercises in Microbiology, 6$^{th}$ Edition, 1988 and Boyd, General Microbiology, 2$^{nd}$ Edition, 1988.

All publications, patent applications, patents, and other references mentioned herein are incorporated by reference in their entirety for all purposes.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Antibody (Ab): A polypeptide that includes at least a light chain or heavy chain immunoglobulin variable region and specifically binds an epitope of an antigen (such as a target agent). Antibodies include monoclonal antibodies, polyclonal antibodies, or fragments of antibodies as well as others known in the art. In some examples, an antibody is specific for a target, such as a particular bacterium or type of bacterium, and thus can be used in a companion assay with the Gram staining methods provided herein.

Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies) and heteroconjugate antibodies (such as, bispecific antibodies). See also, Pierce Catalog and Handbook, 1994-1995 (Pierce Chemical Co., Rockford, Ill.); Kuby, *Immunology*, 3rd Ed., W.H. Freeman & Co., New York, 1997.

A "monoclonal antibody" is an antibody produced by a single clone of B lymphocytes or by a cell into which the light and heavy chain genes of a single antibody have been transfected. Monoclonal antibodies are produced by methods known to those of ordinary skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Bacteria: Prokaryotic organisms that in some examples cause disease (pathogenic bacteria). Bacteria can be classified based on the structural characteristics of their cell walls. For example, the thick layers of peptidoglycan in the "Gram-positive" cell wall stain purple, while the thin "Gram-negative" cell wall appears pink. By combining morphology and Gram-staining, most bacteria can be classified as belonging to one of four groups (Gram-positive cocci, Gram-positive bacilli, Gram-negative cocci and Gram-negative bacilli).

Examples of bacteria that can be detected with the disclosed Gram staining methods, include without limitation: *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii biovar sobria (Aeromonas sobria),* and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis,* and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis,* and *Bordetella bronchiseptica*), *Borrelia* sp. (such as *Borrelia recurrentis,* and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli,* including opportunistic *Escherichia coli,* such as enterotoxigenic *E. coli,* enteroinvasive *E. coli,* enteropathogenic *E. coli,* enterohemorrhagic *E. coli,* enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus*), *Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium intracellulare, Mycobacterium avium, Mycobacterium bovis,* and *Mycobacterium marinum*), *Mycoplasm* sp. (such as *Mycoplasma pneumoniae, Mycoplasma hominis,* and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae,* erythromycin-resistant serotype 14 *Streptococcus pneumoniae,* optochin-resistant serotype 14 *Streptococcus pneumoniae,* rifampicin-resistant serotype 18C *Streptococcus pneumoniae,* tetracycline-resistant serotype 19F *Streptococcus*

*pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* sp. (such as *Yersinia enterocolitica, Yersinia pestis*, and *Yersinia pseudotuberculosis*) and *Xanthomonas maltophilia* among others.

Contact: Placement in direct physical association; includes both in solid and liquid form. For example, contacting can occur in vitro between a reagent (such as a component of a Gram stain) and a sample that is either in solution or on a surface (for example on a microscope slide).

Decolorizing agent: An agent that can substantially remove a primary stain (e.g., crystal violet) and trapping agent (e.g., iodine) complex from a sample (e.g., a sample stained with a primary stain and trapping agent), such as substantial removal of the complex from the cell wall of Gram-negative bacteria, but not Gram-positive bacteria. In one example, such a complex is referred to as a crystal violet-iodine (CV-I) complex. In particular examples, the decolorizing agent is incubated with the sample containing primary stain-trapping agent complexes (e.g., CV-I complexes) for a period of time sufficient to substantially remove the complexes (and thus the primary stain) from the Gram-negative cells (such as at least 90%, at least 95%, or at least 99% complex removal), but not substantially from Gram-positive cells.

Decolorizing formulation: A composition that includes one or more decolorizing agents. A slow-acting decolorizing formation or agent is one that requires longer amounts of time to remove primary stain-trapping agent (e.g., CV-I) complexes (and thus the primary stain, e.g., crystal violet) from the Gram-negative cells, for example an amount of time that permits automated equipment to complete the decolorizing step, thus maintaining the ability of the automated equipment to control completion of the decolorizing step before more decolorizing occurs than is desirable (such as decolorizing Gram-positive bacteria). In some examples, a slow-acting decolorizing formation takes at least 30 seconds, at least 60 seconds, at least 120 seconds, or at least 220 seconds, for example 1 to 4 minutes to remove primary stain-trapping agent (e.g., CV-I) complexes from Gram negative bacteria. Examples include 1,2-propanediol and ethylene glycol. A fast-acting decolorizing agent is one that requires only a short amount of time to remove primary stain-trapping agent (e.g., CV-I) complexes (and thus the primary stain, e.g., crystal violet) from the Gram-negative cells, such as less than 20 seconds, less than 15 seconds, less than 10 seconds, or less than 5 seconds, for example 1 to 2 seconds, 1 to 5 seconds, 1 to 10 seconds or 1 to 20 seconds. Examples include ethyl alcohol, acetone, diethyl ether, methyl ether, blends of ethyl alcohol and acetone, and blends of ethyl alcohol with other alcohols such as methanol or 2-propanol.

Detect: To determine if an agent (such as a signal or particular organism, such as a Gram-positive or Gram-negative bacterium) is present or absent, for example a particular bacterium. In some examples, this can further include quantification. For example, use of the disclosed methods and reagents in particular examples permits reporting of stronger and weaker signals.

Gram-positive bacteria: Bacteria that stain dark blue or violet during Gram staining, and have a thick peptidoglycan layer. Exemplary Gram-positive bacteria include:

*Actinobacteria*
*Actinomyces*
*Actinomyces israelii*
*Bacillales*
*Bacillus*
*Clostridium*
*Clostridium acetobutylicum*
*Clostridium aerotolerans*
*Clostridium argentinense*
*Clostridium baratii*
*Clostridium beijerinckii*
*Clostridium bifermentans*
*Clostridium botulinum*
*Clostridium butyricum*
*Clostridium cadaveris*
*Clostridium cellulolyticum*
*Clostridium chauvoei*
*Clostridium clostridioforme*
*Clostridium colicanis*
*Clostridium difficile*
*Clostridium estertheticum*
*Clostridium fallax*
*Clostridium formicaceticum*
*Clostridium histolyticum*
*Clostridium innocuum*
*Clostridium kluyveri*
*Clostridium ljungdahlii*
*Clostridium novyi*
*Clostridium paraputrificum*
*Clostridium perfringens*
*Clostridium phytofermentans*
*Clostridium piliforme*
*Clostridium ragsdalei*
*Clostridium ramosum*
*Clostridium septicum*
*Clostridium sordellii*
*Clostridium sporogenes*
*Clostridium sticklandii*
*Clostridium tertium*
*Clostridium tetani*
*Clostridium thermosaccharolyticum*
*Clostridium tyrobutyricum*
*Corynebacterium*
*Corynebacterium bovis*
*Corynebacterium diphtheriae*
*Corynebacterium granulosum*
*Corynebacterium jeikeium*
*Corynebacterium minutissimum*
*Corynebacterium renale*
*Enterococcus*
*Lactobacillales*
*Listeria*
*Nocardia*
*Nocardia asteroides*
*Nocardia brasiliensis*
*Propionibacterium acnes*
*Rhodococcus equi*
*Sarcina*
*Solobacterium moorei*
*Staphylococcus*
*Staphylococcus aureus*

| -continued |
|---|
| *Staphylococcus capitis* |
| *Staphylococcus caprae* |
| *Staphylococcus epidermidis* |
| *Staphylococcus haemolyticus* |
| *Staphylococcus hominis* |
| *Staphylococcus lugdunensis* |
| *Staphylococcus muscae* |
| *Staphylococcus nepalensis* |
| *Staphylococcus pettenkoferi* |
| *Staphylococcus saprophyticus* |
| *Staphylococcus succinus* |
| *Staphylococcus warneri* |
| *Staphylococcus xylosus* |
| *Strangles* |
| *Streptococcus* |
| *Streptococcus agalactiae* |
| *Streptococcus anginosus* |
| *Streptococcus bovis* |
| *Streptococcus canis* |
| *Streptococcus iniae* |
| *Streptococcus lactarius* |
| *Streptococcus mitis* |
| *Streptococcus mutans* |
| *Streptococcus oralis* |
| *Streptococcus parasanguinis* |
| *Streptococcus peroris* |
| *Streptococcus pneumoniae* |
| *Streptococcus pyogenes* |
| *Streptococcus ratti* |
| *Streptococcus salivarius* |
| *Streptococcus sanguinis* |
| *Streptococcus sobrinus* |
| *Streptococcus suis* |
| *Streptococcus salivarius thermophilus* |
| *Streptococcus uberis* |
| *Streptococcus vestibularis* |
| *Streptococcus viridans* |

Gram-negative bacteria: Bacteria that loose or do not retain dark blue or violet stain during Gram staining, but instead are colored by a counterstain, such as safranin, and appear pink or ed. Gram-negative bacteria have a thin peptidoglycan layer. Exemplary Gram-negative bacteria include:

| Acetic acid bacteria |
|---|
| *Acinetobacter baumannii* |
| *Agrobacterium tumefaciens* |
| *Anaerobiospirillum* |
| *Bacteroides* |
| *Bacteroides fragilis* |
| *Bdellovibrio* |
| *Brachyspira* |
| *Cardiobacterium hominis* |
| *Coxiella burnetii* |
| *Cyanobacteria* |
| *Cytophaga* |
| *Dialister* |
| *Enterobacter* |
| *Enterobacter cloacae* |
| *Enterobacteriaceae* |
| *Escherichia* |
| *Escherichia coli* |
| *Fusobacterium necrophorum* |
| *Fusobacterium nucleatum* |
| *Fusobacterium polymorphum* |
| *Haemophilus haemolyticus* |
| *Haemophilus influenzae* |
| *Helicobacter* |
| *Helicobacter pylori* |
| *Klebsiella pneumoniae* |
| *Legionella* |
| *Legionella pneumophila* |
| *Leptotrichia buccalis* |
| *Megamonas* |
| *Megasphaera* |

| Acetic acid bacteria |
|---|
| *Moraxella* |
| *Moraxella bovis* |
| *Moraxella catarrhalis* |
| *Moraxella osloensis* |
| *Morganella morganii* |
| *Negativicutes* |
| *Neisseria gonorrhoeae* |
| *Neisseria meningitidis* |
| *Neisseria sicca* |
| *Pectinatus* |
| *Propionispora* |
| *Proteobacteria* |
| *Proteus mirabilis* |
| *Proteus penneri* |
| *Pseudomonas* |
| *Pseudomonas aeruginosa* |
| *Pseudomonas genome database* |
| *Rickettsia rickettsii* |
| *Salmonella* |
| *Salmonella enterica* |
| *Salmonella enterica enterica* |
| *Selenomonadales* |
| *Serratia marcescens* |
| *Shigella* |
| *Spirochaeta* |
| *Spirochaetaceae* |
| *Sporomusa* |
| *Stenotrophomonas* |
| *Streptococcus gordonii* |
| *Vampirococcus* |
| *Verminephrobacter* |
| *Vibrio cholerae* |
| *Wolbachia* |
| *Zymophilus* |

Primary stain: In Gram staining, it is the first dye applied to a sample. An example of a primary stain is crystal violet dye.

Quantitating: Determining or measuring a quantity (such as a relative quantity) of a target, such as the quantity of a target bacterium present in a sample.

Reference value: A number or range of numbers representing a particular condition. An experimental value can be compared to the reference value, for example to make a diagnosis or prognosis. For example, a reference value can be a relative or absolute, maximum or minimum amount (or range) of color expected to define a positive or negative result, such as Gram-positive or Gram-negative.

Slide: Traditionally a substrate used to mount or attach a sample to for microscopy, which is typically but not necessarily transparent to light. Samples may be processed before and/or after mounting onto a slide. In some examples, a slide may be more or less transparent or opaque and made of glass, silica, quartz, or any other material amenable to Gram-staining. A slide may be configured to accommodate one or more specimens from one or more subjects. A slide as used herein also includes non-traditional substrates such as a tape, a disc, a plate, or any other flat, curved, rectangular, or round surface or shape amenable to presenting a sample for Gram-staining.

Subject: Living or deceased multi-cellular organisms, a category that includes plants as well as human and non-human animals, such as veterinary subjects (e.g., birds, cats, dogs, cows, pigs, horses, and rodents). In one example, a subject is known or suspected of having a bacterial infection.

Trapping agent: An agent that forms a complex with a dye and then reduces or slows the extent to which the dye may be rinsed from the sample or substrate. In a Gram stain protocol, Iodine is an example trapping agent. The trapping agent is sometimes referred to as a mordant but is more accurately a trapping agent. A mordant binds more tightly to the substrate and is not easily rinsed out, and in Gram staining, some capacity to be removed through rinsing is required to avoid false positives. A mordant forms a complex with a dye that then additionally binds a substrate, such as a fabric, and then strongly prevents removal of the dye through rinsing. A trapping agent also forms a complex with a dye, but that complex only impedes removal of the dye during rinsing. The mechanism of trapping action is often unknown, but may be due to beneficial retarding of diffusion or steric hindrances. Trapping agents likely do not act through strong bonding with a substrate, and typically a dye in complex with a trapping agent may still be removed under the right conditions, such as through sufficiently long application of a sufficiently strong decolorizing agent, as in Gram staining.

Under conditions sufficient for: A phrase that is used to describe any environment that permits the desired activity. This includes bringing a reagent into contact with a sample under conditions that allow the reagent to physically or chemically interact or react with, diffuse through, or displace other components of the sample. In a specific example, this includes contacting a sample (such as one know or suspected of containing a bacterium) with one or more reagents or components of the Gram stain, to permit accurate detection of Gram-negative or Gram-positive bacteria in the sample.

Overview

The Gram stain is a well known, commonly used microbiological technique for the detection, classification, and identification of microorganisms, especially bacteria, such as the differentiation of bacteria into two general classes based on their cell membrane structures: Gram-positive and Gram-negative. The principal difference between Gram-positive and Gram-negative bacteria is that in Gram-positive bacteria, the primary staining reagents are absorbed within the whole cellular structure, while in the Gram-negative bacteria, staining occurs only superficially. Consequently, when the sample is subsequently treated with a decolorizing agent, Gram-negative bacteria tend to lose their color, while Gram-positive bacteria normally remain stained blue or violet.

The Gram stain is prone to inconsistent and variable results. In particular, the decolorizing step can be problematic with respect to achieving the proper amount of decolorization of the bacteria. If there is not enough decolorizing, Gram-negative bacteria retain the primary stain (e.g., crystal violet), while if there is too much decolorizing, both Gram-positive and Gram-negative bacteria are destained. The inconsistencies in decolorizing can be attributed to the affinity of the primary stain-trapping agent complex for the decolorizing solvent, the amount of decolorizing solvent applied, the relative solubilizing strength of the decolorizing solvent, as well as the amount of time the decolorizing solvent is in contact with the sample.

In traditional manual Gram staining methods the decolorizing step requires only a small volume (such as 2-3 drops) and takes only a few seconds to decolorize the Gram-negative bacteria. Gram stains are conventionally prepared and analyzed manually. However, this is too fast for automated procedures, which due to limitations of the instrumentation, can require minutes at this step. As a result, when traditional decolorizing agents are used in an automated system, an unacceptable amount of decolorizing occurs. Thus, provided herein are new slower-acting decolorizing agents and formulations that prolong the decolorizing step and permit Gram staining to be automated.

Methods of Gram Staining

Gram staining traditionally includes four steps, each of which applies to the sample one of the following reagents: a primary stain, commonly crystal violet dye; a trapping agent (sometimes referred to as a mordant), commonly iodine; a decolorizing agent, commonly ethanol or ethanol/acetone; and a counterstain, usually containing safranin O, fuchsin, or other red dye. The present disclosure provides methods of improving on the prior manual methods of Gram staining that included a very rapid decolorizing step (e.g., 1-5 seconds). The disclosed methods for Gram staining can be used in automated process, as slow-acting decolorizing agents been identified that prolong the decolorizing step (e.g., decolorizing takes at least 30 seconds or at least 60 seconds).

The disclosure provides methods of Gram staining a sample. Such methods can be used to detect and distinguish Gram-positive and Gram-negative bacteria present in the sample. In particular examples, the method includes contacting a sample (or a plurality of samples) with a slow-acting decolorizing formulation under conditions sufficient to remove a primary stain-trapping agent complex (e.g., CV-I complex) from Gram-negative bacteria but not Gram-positive bacteria, wherein the sample was previously contacted with a primary stain and a trapping agent.

It will be appreciated that in some examples, the method further includes one or more other steps of Gram staining. For example, the method can further include one or more of: contacting the sample with a primary stain under conditions sufficient to stain the cell wall (which includes peptidoglycan) (and in some examples the cell membrane) of Gram-positive and Gram-negative bacteria, contacting the sample with a trapping agent under conditions sufficient to form a primary stain-trapping agent complex, which can prevent removal of the primary stain from the Gram-positive bacteria but not Gram-negative bacteria, and contacting the sample with a counterstain under conditions sufficient to stain the cell wall (which includes peptidoglycan) (and in some examples the cell membrane) of decolorized Gram-negative bacteria.

Contacting the sample with a primary stain can include contacting or incubating the sample with a formulation that includes crystal violet (CV) or Gentian violet. In one example, the primary stain formulation includes CV or Gentian violet at a concentration of at least 0.5 g/L, at least 0.75 g/L, at least 1 g/L, at least 2 g/L, at least 3 g/L, at least 4 g/L, or at least 5 g/L, such as 1 to 4 g/L, for example 3 g/L. In some examples, the CV or Gentian violet is present in a solution containing isopropanol, ethanol/methanol, and water, such as 50 ml isopropanol, 50 ml ethanol/methanol, and 900 ml water. In some examples, the CV or Gentian violet solution contains ammonium oxalate to enhance stability.

Contacting the sample with a trapping agent can include contacting or incubating the sample with a formulation that includes iodine, such as Gram iodine or polyvinylpyrrolidone-iodine (PVP-iodine) solution. Gram iodine is a mixture that can include at least 0.1% iodine (e.g., at least 0.2%, at least 0.5%, or at least 1%, such as about 0.1%-1% iodine) and at least 0.1% potassium iodine (e.g., at least 0.2%, at least 0.5%, at least 1%, at least 1.5%, or at least 2%, such as about 0.1%-2% potassium iodine), for example in water or alcohol mixtures. PVP-iodine includes at least 1% polyvinylpyrrolidone (e.g., at least 2%, at least 5%, at least 10%, at least 20%, at least 30%, or at least 35%, such as about 1-35% polyvinylpyrrolidone) and at least 1% iodine (e.g., at least 2%, at least 5%, at least 10%, at least 20%, at least 30%, or at least 35%, such as about 1%-35% iodine) in water (e.g., see U.S. Pat. Nos. 2,739,922 and 3,898,326).

Contacting the sample with a counterstain can include contacting or incubating the sample with a formulation that includes fuchsin (such as basic fuchsin or carbol fuchsin), neutral red, and/or safranin O. In one example, the counterstain formulation includes fuchsin at a concentration of at least 0.01%, at least 0.02%, at least 0.03%, at least 0.05%, at least 0.1%, at least 0.2%, at least 0.3%, at least 0.4%, or at least 0.5%, such as from 0.02% to 0.5%. In one example, the counterstain formulation includes neutral red at a concentration of at least 0.01%, at least 0.02%, at least 0.03%, at least 0.05%, at least 0.1%, at least 0.2%, at least 0.3%, at least 0.4%, or at least 0.5%, such as from 0.02% to 1%. In one example, the counterstain formulation includes safranin O at concentration of at least at 0.1%, such as at least at 0.2%, at least at 0.3%, at least at 0.4%, at least at 0.5%, at least at 0.6%, at least at 0.7%, or at least at 0.8%, such as 0.1% to 1% or 0.1% to 0.8% safranin O. The counterstain can be formulated in water, but in some examples may include 1%-20% ethanol or methanol.

In some examples, the sample is incubated with the slow-acting decolorizing formulation and the counterstain at the same time. In some examples, the concentration of slow-acting decolorizing formulation in a combined slow-acting decolorizing formulation/counterstaining formulation can range from about 75% to 99%, such as at least 75% slow-acting decolorizing formulation, at least 80% slow-acting decolorizing formulation, at least 90% slow-acting decolorizing formulation, or at least 95% slow-acting decolorizing formulation. In other examples, the sample is first incubated with the slow-acting decolorizing formulation followed by the counterstain.

One skilled in the art will appreciate that each contacting step of the Gram stain method can include or be followed by a rinsing step, prior to the next contacting step. Rinsing can be accomplished using any subsequent formulation capable of washing away a previous formulation without an undesirable reaction. For example, the subsequent formulation may be one of the next Gram stain formulations, brought into contact with the sample in excess quantity and allowed to drain away, in which case rinsing is effectively combined with contacting a sample with the next Gram stain formulation (e.g., in the order shown in FIG. 1). In another example, separate rinsing steps are added after or as part of the contacting steps (e.g., those shown in FIG. 1). In this example, rinsing occurs when a sample is contacted with an inactive formulation (e.g., water or buffer), and then allowed to drain away.

In some examples, the amount of time the sample is contacted with or incubated with the slow-acting decolorizing formulation is longer than traditional manual Gram staining. For example, use of a slow-acting decolorizing formulation requires longer amounts of time to remove primary stain-trapping agent (e.g., CV-I) complexes (and thus the primary stain, e.g., crystal violet) from the Gram-negative cells. In some examples, the sample is contacted with or incubated with the slow-acting decolorizing formulation at least 30 seconds, at least 45 seconds, at least 60 seconds, at least 120 seconds, or at least 220 seconds, for example 30 seconds to 4 minutes, 1 to 5 minutes, or 2 to 4 minutes. In some examples, longer periods of decolorizing permit automated equipment to complete the decolorizing step, thus maintaining the ability of the automated equipment to control completion of the decolorizing step before more decolorizing occurs than is desirable (such as decolorizing Gram-positive bacteria). Thus, in some examples, the time between or at one or more steps is designed to conform to automation, such as automation of the Gram stain by a particular piece of equipment.

In one example, the sample is incubated or contacting with the primary stain, trapping agent, or counterstain for at least 30 seconds, at least 40 seconds, at least 50 seconds, at least 60 seconds, at least 70 seconds, at least 80 seconds, at least 90 seconds, at least 100 seconds, at least 120 seconds, at least 150 seconds, at least 180 seconds, at least 210 seconds, at least 220 seconds, at least 240 seconds, at least 270 seconds, or at least 300 seconds. In addition, after contacting a sample with any or each of the Gram stain formulations (primary stain, trapping agent, slow-acting decolorizing formulation and counterstain), subsequent contacting of the sample with a rinse formulation or with any subsequent Gram stain formulation can in some example occur after at least approximately 10 seconds, 20 seconds, 30 seconds, 40 seconds, 50 seconds, 60 seconds, 70 seconds, 80 seconds, 90 seconds, 100 seconds, 120 seconds, 150 seconds, 180 seconds, 210 seconds, 240 seconds, 270 seconds, or 300 seconds have elapsed. Thus for example, after contacting the sample with a primary stain, contacting with the trapping agent can occur at least 10 seconds later, such as at least 30 seconds, or at least 1 minute later. In examples in which separate rinse steps using inactive formulations are included, subsequent to that rinse step, contacting with the next Gram stain formulation can occur after at least approximately 0.5 seconds, 1 second, 2 seconds, 4 seconds, 6 seconds, 8 seconds, 10 seconds, 20 seconds, 30 seconds, 40 seconds, 50 seconds, 60 seconds, 70 seconds, 80 seconds, 90 seconds, 100 seconds, 120 seconds, 150 seconds, 180 seconds, 210 seconds, 240 seconds, 270 seconds, or 300 seconds have elapsed.

The temperature of the reagents used in the Gram staining methods can be ambient or be controlled by automated equipment and local facilities to be the same for each formulation or to vary for one or more formulations. In one example, inactive rinse formulations are relatively colder than ambient air temperature. In some examples, inactive rinse formulations are in the range of 5° to 50° C. immediately prior to being brought into contact with a sample. In some examples, one or more of the Gram stain formulations (primary stain, trapping agent, slow-acting decolorizing formulation and counterstain) are at 10° to 60° C. immediately prior to being brought into contact with a sample.

In some examples, the pH of a Gram stain formulation is adjusted, and can include acids, bases, and buffering agents. In some examples, one or more of the Gram stain formulations (primary stain, trapping agent, slow-acting decolorizing formulation and counterstain) are at pH=3 to pH=8, for example to achieve better staining and for distinguishing bacterial cells from non-bacterial cells following Gram staining.

In some examples, the method further includes detecting the Gram-positive or Gram-negative bacteria in the sample, for example with a microscope or other similar equipment. For example, the method can include determining whether the analyzed sample contains Gram-positive and/or Gram-negative bacteria.

The disclosed methods are exemplified in FIG. 1, which shows an exemplary automated staining method, 100, which includes a Gram staining procedure 101. The Gram stain procedure 101 shown in FIG. 1 has steps that include: contacting the sample with a primary stain formulation 107, contacting the sample with trapping formulation 108, contacting the sample with a slow-acting decolorizing formulation 109, contacting a sample with a counterstain formulation 110, and classifying the sample 111 as Gram-positive, Gram-negative, or indeterminate. Thus, the method includes contacting the sample with the slow-acting decolorizing formulation, 109. FIG. 1 shows that contacting the sample with the slow-acting decolorizing formulation 109 occurs after the sample has been contacted with the primary stain formulation 107 and by the trapping formulation 108, but before contacting the sample with the counterstain formulation 110. As discussed above, each contacting step 107, 108, 109, and 110, can include or be followed by additional rinsing steps, prior to the next contacting step. For example, after the sample is contacted with the primary stain formulation 107, it can be rinsed prior to or during contacting the sample with the trapping formulation 108. The method can also include step 111 of classifying or determining whether the bacteria in the sample are Gram-negative, Gram-positive, or whether it is not possible to make such a determination.

Thus, after contacting a sample with any or each of the Gram stain formulations of FIG. 1 (107, 108, 109, and/or 110), the subsequent contacting with a rinse formulation or with the subsequent Gram stain formulation can occur after at least approximately 10 seconds, 20 seconds, 30 seconds, 40 seconds, 50 seconds, 60 seconds, 70 seconds, 80 seconds, 90 seconds, 100 seconds, 120 seconds, 150 seconds, 180 seconds, 210 seconds, 215 seconds, 220 seconds, 240 seconds, 270 seconds, or 300 seconds have elapsed. In examples in which separate rinse steps using inactive formulations are included, subsequent to that rinse step, contacting with the next Gram stain formulation of FIG. 1 (107, 108, 109, and/or 110) may occur after at least approximately 0.5 seconds, 1 second, 2 seconds, 4 seconds, 6 seconds, 8 seconds, 10 seconds, 20 seconds, 30 seconds, 40 seconds, 50 seconds, 60 seconds, 70 seconds, 80 seconds, 90 seconds, 100 seconds, 120 seconds, 150 seconds, 180 seconds, 210 seconds, 240 seconds, 270 seconds, or 300 seconds have elapsed.

As shown in FIG. 1, in a method for automated Gram staining 100, the method can include steps for obtaining a sample 102 and loading the sample 103 into the automated equipment. The automated equipment may perform assays in parallel 105 or in series preceding 104, or following 106, Gram staining steps 101. Preceding 104 and following series assays 106 can be performed on the same sample, but for example different slides. Examples of preceding 104 and following series assays 106 include immunoassays and additional microbiological assays.

Automation

In some examples, one or more of the Gram staining steps (e.g., contacting a sample with a primary stain formulation, trapping agent formulation, slow-acting decolorizing agent formulation, and/or counterstain formulation) occur using automatic staining equipment. For example, the disclosed methods can be used with Ventana Medical Systems, Inc. equipment such as the Ventana NexES Special Stainer, Ventana BenchMark Special Stainer, Benchmark XT, Benchmark Ultra, and Discovery systems. Exemplary systems are disclosed in U.S. Pat. No. 6,352,861, U.S. Pat. No. 5,654,200, U.S. Pat. No. 6,582,962, U.S. Pat. No. 6,296,809, and U.S. Pat. No. 5,595,707, and additional information concerning automated systems and methods also can be found in PCT/US2009/067042.

In some examples, the method for automated Gram staining is a computer-implemented method in which an algorithm, a computer within the automated equipment, a separate computer, and/or a distributed computer system and/or network contribute to execution of any or all of the Gram staining steps (e.g., one or more of the steps in FIG. 1, such as steps 107, 108, 109, 110, and 111 of FIG. 1) via computer-executable instructions in one or more computer-readable media. For example, computer implementation of the disclosed Gram staining method (e.g., as shown in FIG. 1) may contribute to tracking of samples, selection and/or timing of assays and/or steps of assays, control of equipment, acquisition and/or analysis of results, data retention, reporting to and interface with medical or other information systems, decision making, changes to sample flow, and/or notifications to operators and other personnel.

In automated Gram staining methods, automated equipment may require more time to process multiple samples and proceed than traditional manual Gram staining methods, such as minutes rather than seconds. For example, the decolorizing step can be adjusted in terms of duration, as well as volume and solvating strength, to adequately remove primary stain-trapping agent complex (e.g., CV-I complex) from only the Gram-negative bacteria. However, for automated systems, like the Ventana Medical Systems, Inc. NexES Special Stainer, BenchMark Special Stainer, Benchmark XT, Benchmark Ultra, or Discovery systems, in which the time between dispense/application and rinsing/removal is fixed to definite minimum value, control of the decolorizing step is constrained to changing either the volume or solvating strength of the decolorizing formulation. If the volume is too small, inconsistent decolorizing can occur, and it may not be possible to alter the solvating strength of ethanol to allow for selective decolorizing of the primary stain-trapping agent complex (e.g., CV-I complex) from only the Gram-negative bacteria. For example, the Ventana BenchMark Special Stainer operates within a defined, invariable lockstep between the two processes of dispense and removal, and it is shown herein that slow-acting decolorizing formulations, such as those that include 1,2-propandiol, effectively and selectively decolorizes the Gram-negative bacteria within this timeframe.

The automatic staining equipment may operate in part through the use of compressed air. Thus, in some examples when the sample is contacted with a primary stain formulation, trapping agent formulation, slow-acting decolorizing agent formulation, and/or counterstain formulation, compressed air is used to deliver the primary stain formulation, trapping agent formulation, slow-acting decolorizing agent formulation, and/or counterstain formulation, to the sample.

In some examples the method includes loading the sample to be analyzed for the presence of bacteria into automatic staining equipment.

In a particular example, a method for Gram staining bacteria on a slide using automatic staining equipment is provided. The automatic staining equipment can include a carousel means for holding a plurality of slides, wherein each slide has thereon a sample to be stained, such as a sample known or suspected of containing bacteria. The automatic staining equipment can also include a means for rotating the carousel means at predetermined speeds and a means for directing and controlling application of reagents (such as Gram staining reagents or other stains) onto the slides and samples during rotation of the carousel means. Such a method can include directing a primary stain reagent (such as one containing crystal violet) onto the slides in the carousel to contact the bacteria on the slides with the primary stain reagent; directing water, a water-surfactant mixture, or buffer onto the slides in the carousel to rinse the primary stain reagent from the slides, for example under conditions to permit removal of excess stain; directing a trapping reagent (such as one containing iodine) onto the slides in the carousel to contact the bacteria on the slides with the trapping reagent, for example under conditions to permit formation of a primary stain-trapping agent complex in the Gram-positive bacteria in the sample, directing water or other buffer onto the slides in the carousel to rinse excess trapping reagent from the slides; directing a slow-acting decolorizing formulation and a counterstain, either separately or together, onto the slides in the carousel, for example under conditions to permit removal of primary stain in the Gram-negative bacteria in the sample; and directing water or buffer onto the slides in the carousel to rinse excess slow-acting decolorizing formulation and/or counterstain from the slides (if the slow-acting decolorizing formulation and counterstain are added separately, the method can include a washing step in between). The method can further include detecting the Gram-positive or Gram-negative bacteria on the slide.

Slow-Acting Decolorizing Formulations

The slow-acting decolorizing formulation used in the disclosed methods relies on the identification of slow-acting decolorizing agents such as 1,2-propanediol and ethylene glycol. It is shown herein that the decolorizing agent 1,2-propanediol, or propylene glycol (PG) as it is commonly called, can effectively decolorize the CV-I complex from Gram-negative bacteria within the timed lockstep (4 minutes) of an automated stainer, for example the BenchMark Special Stainer. PG is slower to dissolve the lyposaccharide layer of Gram-negative bacteria and allow diffusion of the CV-I complex from the bacterial cell membrane (peptidoglycan) than other decolorizers, thereby allowing selective decolorizing of only Gram-negative cells to occur at a slower rate. Thus PG allows a Gram stain to be performed by an automated staining system having a set time between decolorizer application and removal that is substantially longer than that used with traditional decolorizers.

One or more of these and any other slow-acting decolorizing agents may be used in pure form, diluted with water or a buffer, or mixed with fast-acting agents in order to create decolorizing formulations of desirable rate of decolorizing. In one example, a slow-acting decolorizing formulation includes a slow-acting decolorizing agent, such as 1,2-propanediol, ethylene glycol, or combinations thereof. In a specific example, the slow-acting decolorizing formulation is or consists of 1,2-propanediol or ethylene glycol. In some examples, water may be included in the slow-acting decolorizing formulation, for example at concentrations ranging from about 0% to 25%, such as 0.5% to 25%, 1% to 20%, 5% to 10%, such as about 10%.

The slow-acting decolorizing formulation can in some examples include a mixture of a slow-acting decolorizing agent and a fast-acting decolorizing agent, such as at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.9% of a slow-acting decolorizing agent (e.g., 1,2-propanediol, ethylene glycol, or combinations thereof), such as 80% to 99.99%, 80% to 95%, 90% to 99, or 90% to 95% of a slow-acting decolorizing agent, and no more than 20%, no more than 19%, no more than 18%, no more than 17%, no more than 16%, no more than 15%, no more than 14%, no more than 13%, no more than 12%, no more than 11%, no more than 10%, no more than 9%, no more than 8%, no more than 7%, no more than 6%, no more than 5%, no more than 4%, no more than 3%, no more than 2%, no more than 1%, no more than 0.5%, or no more than 0.01% of a fast-acting decolorizing agent such as 0.01% to 20%, 1% to 20%, 1% to 10%, or 1% to 5% of a fast-acting decolorizing agent. Examples of fast-acting decolorizing agents include propyleneglycol methyl ether, diethyl ether, ethanol, acetone, methanol, 1-propanol, 2-propanol, 1-butanol, or combinations thereof, such as blends of ethyl alcohol and acetone and blends of ethyl alcohol with other alcohols such as methanol or 2-propanol.

Samples

A sample can be any material to be analyzed for the presence of bacteria. A sample can be biological or non-biological and can be obtained from a subject, an environment, a system, or a process. Thus, in some examples, the method includes obtaining the sample. For example, the sample can be obtained from a subject known or suspected of having a bacterial infection, or from a source known or suspected of being contaminated by bacteria.

In one example the sample is obtained from a subject, such as a human subject. Such a sample can be any solid or fluid sample obtained from, excreted by or secreted by the subject, such as cells, cell lysates, peripheral blood (or a fraction thereof such as serum or plasma), urine, bile, ascites, saliva, cheek swabs, tissue biopsy (such as a tumor biopsy or lymph node biopsy), surgical specimen, bone marrow, amniocentesis samples, fine needle aspirates, cervical samples (for example a PAP smear, cells from exocervix, or endocervix), cerebrospinal fluid, aqueous or vitreous humor, a transudate, an exudate (for example, fluid obtained from an abscess or any other site of infection or inflammation), fluid obtained from a joint (for example, a normal joint or a joint affected by disease, such as a rheumatoid arthritis, osteoarthritis, gout or septic arthritis) and autopsy material.

In one example the sample is obtained from the environment, such as from a body of water, air, sediment, dust, soil, or from the interior or surface of an animate or inanimate object in a natural or a residential, commercial, industrial, medical, academic, agricultural, or other man-made environment (e.g., food processing, production, and consumption facilities and disposal environments), and can be obtained from an industrial source, such as a farm, waste stream, or water source. Thus, samples can be those obtained from any environment known or suspected to harbor bacteria, microorganisms, or multicellular material generally.

In one example the sample is a food sample (such as a meat, fruit, dairy, or vegetable sample) or a sample obtained from a food-processing plant.

In some examples, the sample is a collected fluid, scraping, filtrand, or culture. In one example, the sample is a cytology sample. In particular examples, samples are used directly (e.g., fresh or frozen), or can be manipulated prior to use, for example, by concentration, dilution, fixation (e.g., using formalin or heat) and/or embedding in wax (such as formalin-fixed paraffin-embedded (FFPE) samples). In one example, the sample is heat-fixed to a microscope slide.

Additional Assays

In some examples, the disclosed methods can include performing additional assays on the sample, for example to determine or identify the particular bacteria in the sample. The additional assays can be performed before or after the Gram staining, or even simultaneously or contemporaneously with the Gram staining. Such additional assays are usually performed on a separate slide. For example, a sample can be applied to a plurality of slides (for example different slices or sections of a FFPE sample), wherein each slide is subjected to a particular assay. Thus, multiple assays can be performed in parallel and/or in series on the same sample slide, and/or multiple sections taken from the same sample and mounted on separate slides, and/or on different samples from the same and/or different subjects mounted on the same and/or separate slides.

In one example, the sample is subjected to an immunoassay, for example by incubation with one or more antibodies specific for a particular target bacterium, and detected using a label (such as a label on the antibody or via use of a labeled secondary antibody). Exemplary detectable labels include fluorophores, haptens, enzymes, radiolabels, quantum dots, and others known in the art.

In another example, the sample is subjected to additional microbiological assays. For example, the sample can be contacted with one or more other dyes, such as one or more of the following stains: Acid Fast Bacilli (AFB) III, Alcian Blue, Alcian Blue for Periodic Acid Schiff (PAS), Alcian Yellow, Congo Red, Diastase, Elastic, Giemsa, Grocott's Methenamine Silver stain (GMS) II, iron, Jones Light Green, Jones, Light Green for PAS, Mucicamine PAS, Reticulum, Steiner II, Trichrome Blue, and Trichrome Green. In one example, the sample is contacted with Ziehl-Neelsen or similar stains, for example to detect mycobacteria or *Nocardia*, which show acid-fastness but are sometime difficult to identify with Gram staining.

Kits

Kits that can be used with the disclosed methods are provided herein. In some examples, such kits can be used with an automated Gram staining method having a longer decolorizing step (such as a decolorizing step that takes at least 30 seconds, at least 1 minute, at least 2 minutes, at least 3 minutes, at least 4 minutes, or at least 5 minutes to complete).

In particular examples, the disclosed kits include a slow-acting decolorizing formulation in a container (e.g., vial or vessel). The kits can in some examples also include reagents for performing one or more of the other steps of the Gram stain method. For example, kits can further include a primary stain formulation, a trapping agent formulation, and/or a counterstain formulation, for example wherein each formulation is in a separate container.

In one example, the container of the slow-acting decolorizing formulation includes one or more slow-acting decolorizing agents, such as 1,2-propanediol, ethylene glycol, or combinations thereof. In a specific example, the slow-acting decolorizing formulation is or consists of 1,2-propanediol or ethylene glycol. The slow-acting decolorizing formulation can in some examples include a mixture of a slow-acting decolorizing agent(s) and a fast-acting decolorizing agent(s), such as at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.9% of one or more slow-acting decolorizing agents (e.g., 1,2-propanediol, ethyl glycol, or combinations thereof), such as 80% to 99.99%, 80% to 99%, 80% to 90%, 90% to 99.9%, or 90% to 98%, of a slow-acting decolorizing agent, and no more than 20%, no more than 19%, no more than 18%, no more than 17%, no more than 16%, no more than 15%, no more than 14%, no more than 13%, no more than 12%, no more than 11%, no more than 10%, no more than 9%, no more than 8%, no more than 7%, no more than 6%, no more than 5%, no more than 4%, no more than 3%, no more than 2%, no more than 1%, no more than 0.5%, or no more than 0.01% of one or more fast-acting decolorizing agents (e.g., propyleneglycol methyl ether, diethyl ether, ethanol, acetone, methanol, 1-propanol, 2-propanol, 1-butanol, or combinations thereof, such as blends of ethyl alcohol and acetone and blends of ethyl alcohol with other alcohols such as methanol or 2-propanol), such as 0.01% to 20%, 0.1% to 20%, 0.1% to 10%, 1% to 20%, or 1% to 10%, of a fast-acting decolorizing agent.

In one example, the container of the primary stain formulation includes crystal violet (CV) or Gentian violet. In one example, the primary stain formulation includes crystal violet at a concentration of at least 0.5 g/L, at least 0.75 g/L, at least 1 g/L, at least 2 g/L, at least 3 g/L, at least 4 g/L, or at least 5 g/L, such as 1 to 4 g/L, for example 3/L. In some examples, the CV is present in a solution containing isopropanol, ethanol/methanol, and water, such as 50 ml isopropanol, 50 ml ethanol/methanol, and 900 ml water. In some examples, the CV or Gentian violet solution contains ammonium oxalate to enhance stability.

In one example, the container of the trapping agent formulation includes iodine, such as Gram iodine or polyvinylpyrrolidone-iodine (PVP-iodine) solution. Gram iodine can in some examples include at least 0.1% iodine (e.g., at least 0.2%, at least 0.5%, or at least 1%, such as about 0.1%-1% iodine) and at least 0.1% potassium iodide (e.g., at least 0.2%, at least 0.5%, at least 1%, at least 1.5%, or at least 2%, such as about 0.1%-2% potassium iodide), for example in water or alcohol mixtures. PVP-iodine can in some examples include at least 1% polyvinylpyrrolidone (e.g., at least 2%, at least 5%, at least 10%, at least 20%, at least 30%, or at least 35%, such as about 1-35% polyvinylpyrrolidone) and at least 1% iodine (e.g., at least 2%, at least 5%, at least 10%, at least 20%, at least 30%, or at least 35%, such as about 1%-35% iodine) in water (e.g., see U.S. Pat. Nos. 2,739,922 and 3,898,326)

In one example, the container of the counterstain formulation includes fuchsin (such as carbol fuchsin or basic fuchsin), neutral red, and/or safranin 0. In one example, the aqueous counterstain formulation includes fuchsin at a concentration of at least 0.01%, at least 0.02%, at least 0.03%, at least 0.05%, at least 0.1%, at least 0.2%, at least 0.3%, at least 0.4%, or at least 0.5%, such as from 0.02% to 0.50%. In one example, the counterstain formulation includes neutral red at a concentration of at least 0.01%, at least 0.02%, at least 0.03%, at least 0.05%, at least 0.1%, at least 0.2%, at least 0.3%, at least 0.4%, or at least 0.5%, such as from 0.02% to 1%. In one example, the counterstain formulation includes safranin 0 at concentration of at least at 0.1%, such as at least at 0.2%, at least at 0.3%, at least at 0.4%, at least at 0.5%, at least at 0.6%, at least at 0.7%, or at least at 0.8%, such as 0.1% to 1% or 0.1% to 0.8% safranin 0. The counterstain can be formulated in water, but in some examples may include 1%-20% ethanol or methanol.

In some examples, the containers or vessels that include the primary stain formulation, trapping agent formulation, slow-acting decolorizing agent formulation, and/or counterstain formulation, are configured or shaped for loading into automatic staining equipment. For example, the containers can be configured to be used with Ventana Medical Systems, Inc. equipment such as the NexES Special Stainer or a Ventana BenchMark Special Stainer. In some examples, the containers are configured to be used with the Benchmark XT, Benchmark Ultra, or Discovery system, such as those disclosed in U.S. Pat. No. 6,352,861, U.S. Pat. No. 5,654,200, U.S. Pat. No. 6,582,962, U.S. Pat. No. 6,296,809, and U.S. Pat. No. 5,595,707, all of which are incorporated herein by reference. Additional information concerning automated systems and methods also can be found in PCT/US2009/067042, which is incorporated herein by reference. In one example, the container is a chemically resistant polypropylene/polyethylene vial, such as a Ventana BenchMark dispenser.

The kits may also include one or more microscope slides, such as slide suitable for mounting and in some examples fixing a sample, as well as coverslips, pipettes, or combinations thereof.

The kit can optionally also include control slides for verifying the reagents and proper implementation of the Gram stain protocol. For example, one set of control slides can include Gram-positive bacteria, such as *Staphylococcus aureus* (or any of those listed herein), and another set of control slides can include Gram-negative bacteria, such as *Escherichia coli* (or any of those listed herein). In some examples, a control slide in the kit includes no bacteria.

The kit can optionally further include additional reagents for performing additional assays. For example, the kit can include one or more vessels or containers that contain other dyes or stains, such as containers that include one or more of the following stains: Acid Fast Bacilli (AFB) III, Alcian Blue, Alcian Blue for Periodic Acid Schiff (PAS), Alcian Yellow, Congo Red, Diastase, Elastic, Giemsa, Grocott's Methenamine Silver stain (GMS) II, iron, Jones Light Green, Jones, Light Green for PAS, Mucicamine PAS, Reticulum, Steiner II, Trichrome Blue, and Trichrome Green.

In one example, the kit can include a vessel or container that contains bacteria-specific antibodies. In some examples, the kit includes a vessel or container that contains labeled secondary antibodies (e.g., labeled with a fluorophore or quantum dot).

Slow-Acting Decolorizing Compositions

The disclosure also provides slow-acting decolorizing formulations that can be used in the kits and methods provided herein. In one example, the slow-acting decolorizing formulation includes a mixture of both a slow-acting decolorizing agent, and a fast-acting decolorizing agent, such as one or more slow-acting decolorizing agents and one or more fast-acting decolorizing agents.

In one example, the slow-acting decolorizing formulation includes one or more slow-acting decolorizing agents, such as at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.9% of one or more slow-acting decolorizing agents (e.g., 1,2-propanediol, ethylene glycol, or combinations thereof), such as 80% to 99.99% of one or more slow-acting decolorizing agents. In one example, the slow-acting decolorizing formulation includes one or more fast-acting decolorizing agents, such as no more than 20%, no more than 19%, no more than 18%, no more than 17%, no more than 16%, no more than 15%, no more than 14%, no more than 13%, no more than 12%, no more than 11%, no more than 10%, no more than 9%, no more than 8%, no more than 7%, no more than 6%, no more than 5%, no more than 4%, no more than 3%, no more than 2%, no more than 1%, no more than 0.5%, or no more than 0.01% of one or more fast-acting decolorizing agents (e.g., propyleneglycol methyl ether, diethyl ether, ethanol, acetone, methanol, 1-propanol, 2-propanol, 1-butanol, or combinations thereof, such as blends of ethyl alcohol and acetone and blends of ethyl alcohol with other alcohols such as methanol or 2-propanol), such as 0.01% to 20%, 0.1% to 20%, 0.1% to 10%, 1% to 20%, or 1% to 10%, of a fast-acting decolorizing agent.

EXAMPLE 1

Comparison of Gram Staining Decolorizing Agents

This example describes methods used to compare decolorizing agents in Gram staining in order to optimize the rate of decolorization. Crystal Violet and Gram Iodine were prepared according to the procedure of Carson F, Hladik C. Histotechnology: A Self Instructional Text, 3rd edition, pp. 231-233. Hong Kong: American Society for Clinical Pathology Press; 2009 (incorporated herein as reference).

Paraffin embedded tissue sections of Gram-positive controls were deparaffinized using standard histological techniques. These were then stained on an automated prototype stainer in which the crystal violet was dispensed dropwise (~90 μL per drop) on the horizontally positioned tissue section, allowed to incubate for approximately 4 minutes, and then rinsed with an aqueous surfactant solution. Gram iodine was then applied dropwise to the section and this was incubated for about 4 minutes followed by rinsing. At this point, the decolorizing solvent was added to the tissue section manually using a calibrated pipette, followed by manually rinsing with the aqueous surfactant solution at specified time periods. A counterstain of Carbol Fuchsin and Tartrazine was then applied manually (90 and 15 sec incubations, respectively). The slides were then dehydrated and cleared to xylenes, followed by coverslipping with permanent mounting media. Examination under a microscope (20-200×) enabled evaluation of the selectivity of the solvent for decolorizing the Gram (−) bacteria. The results are shown in the table below.

| Solvent | Type | Incubation time | Result* |
| --- | --- | --- | --- |
| 1,2-propanediol (PG) | invention | 210 sec | +/0 |
| 1,2-propanediol (PG) | invention | 60 sec | + |
| 1,2-propanediol (PG) | invention | 30 sec | + |
| 50% PG/50% propyleneglycol methyl ether | invention | 57 sec | 0 |
| 50% PG/50% propyleneglycol methyl ether | invention | 74 sec | 0 |
| 80% PG/20% propyleneglycol methyl ether | invention | 74 sec | + |
| 2-propanol | comparative | 20 sec | − |

*+ = Gram (−) are red, Gram (+) are blue; 0 = minor decolorization of Gram (+); − = gram (+) bacteria decolorized In view of the many possible embodiments to which the principles of the disclosure may be applied, it should be recognized that the illustrated embodiment is only an example of the disclosure and should not be taken as limiting the scope of the invention. Rather, the scope of the disclosure is defined by the following claims. We therefore claim as our invention all that comes within the scope and spirit of these claims.

We claim:

1. A method for Gram staining bacteria on a slide using automatic staining equipment, wherein the automatic staining equipment comprises:
   carousel means for holding a plurality of slides, each slide having thereon a sample to be stained;
   means for rotating the carousel means at predetermined speeds; and
   means for directing and controlling application of reagents onto the slides and samples during rotation of the carousel means,
   and wherein the method comprises:
   directing a crystal violet reagent onto the slides in the carousel to contact the bacteria on the slides with the crystal violet reagent;
   directing water, aqueous buffer, or aqueous detergent, onto the slides in the carousel to rinse the crystal violet reagent from the slides;
   directing iodine reagent onto the slides in the carousel to contact the bacteria on the slides with the iodine reagent;
   directing water, aqueous buffer, or aqueous detergent, onto the slides in the carousel to rinse iodine reagent from the slides;
   directing a slow-acting decolorizing formulation and a counterstain,
   simultaneously or separately, onto the slides in the carousel, wherein the slow-acting decolorizing formulation comprises a slow acting decolorizing agent selected from the group consisting of 1,2-propanediol, ethylene glycol, and mixtures thereof, and wherein the slow-acting decolorizing formulation takes at least 60 seconds to remove the crystal violet reagent and the iodine reagent from a Gram negative bacteria; and directing water, aqueous buffer, or aqueous detergent, onto the slides in the carousel to rinse the slow-acting decolorizing formulation and the counterstain from the slides, wherein at least 180 seconds elapse between the step of directing a slow-acting decolorizing formulation and a counterstain, simultaneously or separately, onto the slides in the carousel and the step of directing water, aqueous buffer, or aqueous detergent, onto the slides in the carousel to rinse the slow-acting decolorizing formulation and the counterstain from the slides.

2. The method of claim 1, wherein directing the counterstain follows directing the slow-acting decolorizing formulation by at least 30 seconds.

3. The method of claim 1, wherein the sample is contacted with the slow-acting decolorizing formulation for at least 220 seconds.

4. The method of claim 1, wherein directing the slow-acting decolorizing formulation and the counterstain, simultaneously or separately is by using compressed air.

5. The method of claim 1, wherein the slow-acting decolorizing formulation further comprises a fast-acting decolorizing agent.

6. The method of claim 5, wherein the slow-acting decolorizing formulation comprises at least 80% of the slow-acting decolorizing agent and no more than 20% of the fast-acting decolorizing agent.

7. The method of claim 5, wherein the slow-acting decolorizing agent is 1,2-propanediol.

8. The method of claim 1, wherein the sample is obtained from a subject known or suspected of having a bacterial infection.

9. The method of claim 1, wherein the sample is an environmental sample or a food sample.

10. The method of claim 1, wherein the sample has been, is simultaneously, or will be subjected to one or more additional assays on the same or separate slides.

11. The method of claim 10, wherein the sample is contacted with one or more antibodies for a specific bacterium, contacted with another stain, or combinations thereof.

12. The method of claim 1, wherein the method further comprises detecting Gram-positive or Gram-negative bacteria.

13. The method of claim 1, wherein the method is a computer-implemented method.

14. The method of claim 1, wherein at least 210 seconds elapse between the step of directing a slow-acting decolorizing formulation and a counterstain, simultaneously or separately, onto the slides in the carousel and the step of directing water, aqueous buffer, or aqueous detergent, onto the slides in the carousel to rinse the slow-acting decolorizing formulation and the counterstain from the slides.

15. The method of claim 1, wherein at least 240 seconds elapse between the step of directing a slow-acting decolorizing formulation and a counterstain, simultaneously or separately, onto the slides in the carousel and the step of directing water, aqueous buffer, or aqueous detergent, onto the slides in the carousel to rinse the slow-acting decolorizing formulation and the counterstain from the slides.

16. The method of claim 1, wherein at least 300 seconds elapse between the step of directing a slow-acting decolorizing formulation and a counterstain, simultaneously or separately, onto the slides in the carousel and the step of directing water, aqueous buffer, or aqueous detergent, onto the slides in the carousel to rinse the slow-acting decolorizing formulation and the counterstain from the slides.

17. The method of claim 1, wherein the slow-acting decolorizing agent is 1,2-propanediol.

18. The method of claim 1, wherein the slow-acting decolorizing formulation consists of 1,2-propanediol.

* * * * *